(12) United States Patent
Li et al.

(10) Patent No.: US 11,970,728 B2
(45) Date of Patent: Apr. 30, 2024

(54) **METHOD FOR INDOORS AND RAPIDLY IDENTIFYING THE RESISTANCE OF WHEAT TO BLACK POINT DISEASE CAUSED BY *BIPOLARIS SOROKINIANA***

(71) Applicant: Henan Agricultural University, Zhengzhou (CN)

(72) Inventors: Qiaoyun Li, Zhengzhou (CN); Guihong Yin, Zhengzhou (CN); Haiyong Li, Zhengzhou (CN); Yumei Jiang, Zhengzhou (CN); Jishan Niu, Zhengzhou (CN); Mengyu Li, Zhengzhou (CN); Siyu Wang, Zhengzhou (CN); Kaige Xu, Zhengzhou (CN)

(73) Assignee: Henan Agricultural University, Zhengzhou (CN)

( * ) Notice: Subject to any disclaimer, the term of this patent is extended or adjusted under 35 U.S.C. 154(b) by 422 days.

(21) Appl. No.: 17/232,480

(22) Filed: Apr. 16, 2021

(65) Prior Publication Data

US 2021/0324440 A1 Oct. 21, 2021

(30) Foreign Application Priority Data

Apr. 17, 2020 (CN) .......................... 202010303314.4

(51) Int. Cl.
*C12Q 1/00* (2006.01)
*A01C 1/00* (2006.01)
*A01G 31/00* (2018.01)
*C12Q 1/18* (2006.01)

(52) U.S. Cl.
CPC .................. *C12Q 1/18* (2013.01); *A01C 1/00* (2013.01); *A01G 31/00* (2013.01)

(58) Field of Classification Search
CPC .............. C12Q 1/18; A01C 1/00; A01G 31/00
See application file for complete search history.

(56) References Cited

PUBLICATIONS

Li et al. 2019 (The correlation between wheat black point and agronomic traits in the North China Plain; Crop Protection 9:17-23) (Year: 2019).*

Liatukas et al. 2011 (Resistance of European winter wheat cultivars to spot blotch at juvenile growth stages; Phytopathol. Mediterr. 50: 350-358) (Year: 2011).*

* cited by examiner

*Primary Examiner* — Albert M Navarro
(74) *Attorney, Agent, or Firm* — Fish IP Law, LLP

(57) ABSTRACT

The present application discloses a method for rapidly identifying the resistance of wheat to black point disease caused by *Bipolaris sorokiniana*, where testing takes places in an indoor, controlled environment. The test method includes surface sterilization of wheat seeds, and cultivating wheat seedlings from the sterilized wheat seeds; preparing conidial suspension of *Bipolaris sorokiniana*, and spraying the conidial suspension on the seedlings at one-leaf-one-shoot stage; recording the percentage of the diseased leaf area in total leaf area of the first leaf of the wheat seedling on the $10^{th}$ day of inoculation; calculating the black point incidence of the wheat according to an equation, and then evaluating the resistance of wheat to black point disease caused by *Bipolaris sorokiniana* through the black point incidence. Compared with existing field identification methods, the method of the present disclosure shortens identification time, simplifies identification procedure, greatly improves identification efficiency, and improves the accuracy and reliability of identification results.

7 Claims, 2 Drawing Sheets

METHOD FOR INDOORS AND RAPIDLY IDENTIFYING THE RESISTANCE OF WHEAT TO BLACK POINT DISEASE CAUSED BY *BIPOLARIS SOROKINIANA*

CROSS REFERENCE TO RELATED APPLICATION

This disclosure claims the priority of Chinese Patent Application NO. 202010303314.4 entitled Method for indoors and rapidly identifying the resistance of wheat to black point disease caused by *Bipolaris sorokiniana* filed with the China National Intellectual Property Administration on Apr. 17, 2020, which is incorporated herein by reference in its entirety.

TECHNICAL FIELD

The present disclosure belongs to the technical field of crop disease detection, and in particular relates to a method for rapidly identifying the resistance of wheat to black point disease caused by *Bipolaris sorokiniana* in an indoor, controlled environment.

BACKGROUND

Black point disease is a common disease in wheat, and it refers to brown or black point with different shapes and to different degrees on surface of wheat grains. Wheat black point disease not only affects the appearance and quality of the wheat grains, leading to a decrease in the level of wheat acquisition, but also affects the seedling emergence rate and seedling growth. More seriously, some pathogens of the black point disease can produce toxins, which seriously affect human health. The severity of the black point disease varies from wheat cultivars, locations, years and prevention measures, the black point incidence generally varies from 0.1% to 70.0% (see Literature 1: Li Q Y, Xu Q Q, Jiang Y M, et al. Correlation between the wheat black point and the agronomic traits in the North China Plain. Crop Prot, 2019, 119; 17-23; Literature 2: Liu J D, He Z H, Wu L, et al. Genome wide linkage mapping of QTL for black point reaction in bread wheat (*Triticum aestivum* L.). Theor Appl Genet, 2016, 129: 2179-2190. Literature 3: Yang G Q, Song Y L, He W L, et al. Control effect of 13 fungicides on wheat black point disease. Plant Protection, 2012, 38: 171-173). Each country has its stringent restrictions on the black point incidence of wheat seeds. The China national standard for wheat (GB 1351-2008) stipulates that the percentage of imperfect grains of third-grade and above is ≤6%, among which, black point grain is considered as one of the six types of imperfect grains. The Huanghuai wheat growth area is a core wheat production area in China. The wheat planting area and annual output account for more than 50% of the country's output. However, the wheat cultivars currently planted in this area are generally susceptible to black point disease. In 2000, the diseased area affected by wheat black point disease merely in Henan province reached more than 3,300 thousand hectares, and commercial grains were generally reduced by 1-2 grades. Farmers in the province suffered a loss more than 1 billion RMB due to the black point disease in wheat (Wang H W, The development of an expert system for early warning and prevention of wheat black point disease in Henan Province. Master's thesis of Henan Agricultural University. 2006, Zhengzhou). It can be seen that wheat black point disease has become one of the urgent problems in wheat production.

Breeding of disease-resistant wheat cultivars is the most economical and effective method to prevent and control black point disease, and identification technology for black point resistance is the basis for disease-resistant breeding and disease control. Since wheat black point develops during the grain filling stage, the identification of wheat resistance to black point can only be carried out during the grain filling stage. At present, the identification of the resistance of wheat cultivars to black point disease is mainly based on the incidence under natural field condition, and the identification is also carried out by inoculating pathogen under controlled field conditions. No matter what identification methods are used, black point survey and evaluation of resistance can be conducted at the time only when the wheat grain filling stage begins and after the grain are harvested (Kang Y B, Liu S T, Cheng Y M, et al, Wheat resistance to black point disease and effect of black point on yield loss. Plant Protection, 1999, 3:25-27; Li Q Y, Xu Q Q, Jiang Y M, et al. Correlation between the wheat black point and the agronomic traits in the North China Plain. Crop Prot, 2019, 119: 17-23). Therefore, the identification can only be conducted once in a wheat growth season (approximately 220 days in the Huanghuai wheat growth area of China, spanning two natural years), which not only lasts for a long time, but also entails going through the processes such as inoculation, moisturizing, and threshing, which represents substantial financial consumption and labor-consuming. In addition, the occurrence and development of wheat black point disease are affected by various factors such as pathogen types and environmental conditions. The incidence for the same wheat cultivar varies greatly in different years and in different locations. Therefore, the stability of evaluating black point resistance under natural field conditions is poor.

The problems of being time-consuming, laborious, and unstable results in the identification of wheat resistance to black point disease have seriously affected the research progress of black point disease resistance breeding and mechanism of disease resistance. *Bipolaris sorokiniana* is a major pathogen causing black point disease in wheat (Xu K G, Jiang Y M, Y K Li, et al. Identification and pathogenicity of fungal pathogens causing black point in wheat on the North China plain, Indian J Microbio, 2018, 58 (2), 159-164), this pathogen not only causes black point disease (symptoms are more serious than other pathogens; in addition to the blackening of the kernels, it also causes decrease in the grain number per panicle, the shrinkage of the kernels, reduction in yield caused by the decrease in weight per thousand grains, and the toxin residue in susceptible grains, etc.), but also is the main pathogen of wheat leaf blight. That is, it affects the wheat grains and causes black point disease, and the infected leaves may cause wheat leaf blight. The leaf blight due to the infection with *B. sorokiniana* can also occur at the seedling stage. The correlation analysis between the seedling leaf blight and the black point disease of the grain caused by *B. sorokiniana* was carried out, and regression analysis was performed on the basis of the significant correlation between them. The black point incidence is calculated by using the percentage of diseased area of leaf blight at the seedling stage through the regression equation, which not only shortens the time for identification of wheat black point resistance, but also avoids the steps of bagging isolation and threshing. In addition, because the experiment is conducted in a controlled, indoor environment, the experimental conditions are easier to control, thus making the experimental results more stable and the identification of wheat black point resistance are faster and the results are more stable.

SUMMARY OF THE DISCLOSURE

In view of the shortcomings of being time-consuming, laborious and unstable results in the prior method for identifying the resistance of wheat to *B. sorokiniana*, the present disclosure provides a method for calculating the black point incidence by identifying, in an indoor controlled environment, the percentage of diseased area of the leaf blight caused by *B. sorokiniana* at seedling stage in wheat, with the significant correlation between percentage of diseased area of the leaf blight and the black point incidence caused by *B. sorokiniana* being the starting point. That is, the present disclosure provides a method for indoors and rapidly identifying the resistance of wheat to black point disease caused by *B. sorokiniana*. Compared with the existing identification methods, the identification method of the present disclosure shortens the time for identification, simplifies identification procedure, and greatly improves identification efficiency, the accuracy and reliability of identification results.

In order to solve the above-mentioned problems, the following technical solution is used in the present disclosure.

The present disclosure provides a method for rapidly identifying the resistance of wheat to black point disease caused by *B. sorokiniana* in an indoor, controlled environment. The method for rapid indoor identification includes the following steps:

a) surface sterilization of wheat seeds:
  selecting healthy and full wheat seeds and immersing the wheat seeds in alcohol, and rinsing the wheat seeds with sterilized distilled water after immersion;

b) cultivating wheat seedlings:
  placing the wheat seeds subject to surface sterilization treatment in step a) in Petri dishes, and placing the Petri dishes in an incubator for 10 days;

c) preparing conidial suspensions of *Bipolaris sorokiniana*:
  cutting the *B. sorokiniana* that have been stored in a refrigerator at 4° C. into 0.3 cm² pieces and inoculating in a potato dextrose agar medium, culturing at 25° C. in the dark, then gently scraping the conidia from the cultured colony by using a glass slide, rinsing the Petri dishes with distilled water, and filtering the mycelial fragments with gauze to obtain a conidial suspension;

d) inoculation with *B. sorokiniana*:
  shaking the *B. sorokiniana* conidial suspension obtained in step c) and spraying the conidial suspension on the leaves of wheat seedlings which has grown to a one-leaf-one-shoot stage in step b), then covering the seedlings with a transparent plastic cover and placing them in an incubator and culturing for 10 days at 25° C.;

e) recording identification results:
  recording the percentage of diseased leaf area in the total leaf area of the first leaf of wheat seedling cultivated in step d) on the 10$^{th}$ day of inoculation to obtain a percentage of the diseased area;

f) calculating black point incidence in wheat:
  calculating the percentage of black point grains, namely the black point incidence, from the percentage of leaf blight area by using the equation y=−1.0037x+66.1360; wherein in the equation, y and x are the black point incidence and the percentage of diseased area, respectively;

g) evaluating resistance to disease:
  evaluating the resistance of wheat to black point disease caused by *B. sorokiniana* based on the black point incidence calculated in step f).

According to one embodiment of method of the present disclosure, wherein in step a), the volume percentage of alcohol in step a) is 70%, the duration of time for the immersion in the alcohol is 2 minutes; the wheat seeds are washed with sterilized distilled water for 3 times.

According to one embodiment of method of the present disclosure, wherein in step a), when rinsing the wheat seeds with sterilized distilled water, adding the distilled water and shaking gently for 5 seconds so as to dissolve the alcohol on the surface of the seeds in the distilled water to prevent the alcohol from inhibiting the germination of wheat seeds.

According to one embodiment of method of the present disclosure, wherein in step b), the step of cultivating the wheat seedlings comprises steps of:

i). placing the wheat seeds in Petri dishes with a diameter of 9 cm, in which Petri dishes 2 layers of sterilized filter paper and 4 mL of sterilized distilled water have been added in advance, and placing 5 wheat cultivar in each Petri dishes with 15 grains for each cultivar;

ii). placing the Petri dishes with the seeds in a 25° C. incubator and culturing the seeds for 3 days in the dark, picking out the wheat seeds with inconsistent germinability, and then adding 10 mL of sterilized distilled water in each Petri dishes, and removing the cover of the Petri dishes;

iii). alternating a temperature and light cycle in the incubator between "25° C., light, 11 hours" and "21° C., dark, 13 hours" after 3 days of the culturing, and then continuing to incubate the seedling for another 7 days.

According to one embodiment of method of the present disclosure, wherein, in step c), after incubating the *B. sorokiniana* at 25° C. in the dark for 7 days, observing the situation of conidia production; a gray color of colonies indicates a low yield of spore production, entailing the removal of the sealing film of the Petri dishes and continuing the culture process; taking out the Petri dishes when the colonies become dark and a large number of conidia are produced.

According to one embodiment of method of the present disclosure, wherein in step c), the step of rinsing the Petri dishes with distilled water and filtering with gauze comprises washing the Petri dishes with distilled water for 2-3 times, and filtering mycelial fragment through four-layer gauze, detecting the concentration of the conidia suspension by using a hemocytometer and adjusting the spore concentration to $1\times10^5$/mL.

According to one embodiment of method of the present disclosure, wherein in the step d) of culturing the seedlings by placing the wheat in an incubator comprises the following steps: firstly incubating the seedlings in the dark for 24 hours, and then setting the temperature and light cycle of the incubator at "25° C., light, 11 hours" and "25° C., dark, 13 hours" alternately; using a hand sprayer to spray 3 mL of sterilized distilled water evenly into the cover twice a day in the morning and in the evening during the culturing process so as to maintain a high humidity required for infection of *Bipolaris sorokiniana* and development of leaf blight.

According to one embodiment of method of the present disclosure, wherein method for evaluating the resistance of wheat to black point disease in step g) comprises: recording as I if there are no diseased grains, which is considered to be immune; recording as HR if the black point incidence is from 0.1% to 1.9%, which is considered to be highly resistant; recording as R if the black point incidence is from 2.0% to 4.9%, which is considered to be resistant; recording as SS if the black point incidence is from 5.0% to 14.9%, which is considered to be slightly susceptible; recording as MS if the black point incidence is from 15.0% to 30.0%, which is considered to be moderately susceptible; and recording as HS if the black point incidence is greater than 30%, which is considered to be highly susceptible.

The equation used in the technical scheme of the present disclosure is y=−1.0037x+66.1360. Correlation analysis is conducted between the percentage of diseased leaf area of leaf blight at seedling stage and black point incidence caused by *B. sorokiniana*. Regression analysis is performed on the basis of a significant correlation between diseased leaf area of leaf blight at seedling stage and black point incidence. In the method of the present disclosure, the correlation coefficient (r) between the percentage of disease leaf area of leaf blight caused by *B. sorokiniana* at the seedling stage of wheat and the black point incidence is −0.95, and the coefficient of determination ($r^2$) of the equation for calculating black point incidence based on the diseased leaf area is 0.90.

The technical scheme of the present disclosure comprises the steps of sterilizing the surface of wheat seeds, placing them in an incubator and cultivating them to the one-leaf-one-shoot stage, then spraying conidial suspension of *B. sorokiniana* and bagging them for maintaining the moisture. After 10 days, the percentage of the diseased area of leaf blight was investigated. By using the regression equation between the percentage of the diseased leaf area of—caused by leaf blight and black point incidence, the black point incidence was calculated, and then the resistance of wheat to black point disease caused by *B. sorokiniana* was evaluated based on the calculated black point incidence. Compared with the existing field identification methods, the identification method of the present disclosure shortens identification time, simplifies identification procedure, greatly improves identification efficiency, and improves the accuracy and reliability of identification results.

In the technical scheme of the present disclosure, based on the internal relationship between the leaf blight caused by *B. sorokiniana* at the wheat seedling stage and black point disease of the grains, it is proposed for the first time to calculate the black point incidence using the percentage of diseased leaf area of leaf blight caused by *B. sorokiniana*. The present disclosure starts with the two pathogenic factors of the concentration of conidia suspension and the time of investigation, and optimizes the concentration of the conidia suspension ($1\times10^5$) used for wheat seedling inoculation and the time for investigating the area of leaf blight in wheat seedling (10 days after inoculation), which not only provides suitable conditions for the leaf blight caused by *B. sorokiniana*, but also shortens the identification time as much as possible.

Positive and Beneficial Effects Brought by the Present Disclosure

*B. sorokiniana* is the major pathogen of the black point disease of wheat, which is widely found in wheat production areas. Without accurate identification of the cultivar resistance, it is impossible to conduct the research on the specialized disease resistance of wheat to this pathogen and carry out disease resistance breeding. At present, the conventional identification methods can only be carried out at the beginning of the wheat grain-filling stage and after the grains are harvested. Those methods last for one month and are carried out once a year. Since the results of the identification in the current year must be investigated after the harvest, the identified resistant materials can only be used in cross breeding in the following year, which consumes valuable research and breeding time. And the field environment, especially the weather conditions beyond human control, is changeable, resulting in a deviation in the identification results between different years. In addition, the conventional field identification methods for wheat black point resistance include tedious procedures of planting, preventing contamination, inoculation, bagging, harvesting, threshing, investigation, and etc. requiring a lot of manpower and material resources. Compared with conventional field identification methods, the present disclosure identifies the resistance to black point caused by *B. sorokiniana* through the black point incidence calculated using the diseased leaf area of leaf blight at the seedling stage, and its prominent beneficial effects are as follows:

Identification Time not being Subject to Seasonal Restrictions

The field identification of resistance to black point disease can only be conducted in the grain filling stage (from the end of April to the beginning of May in Huanghuai wheat growth area of China), while the method of the present disclosure is not limited by seasons. The cultivation of wheat seedlings in the incubator can be carried out all year round, and *B. sorokiniana* can be cultured all year round. Wheat leaf blight caused by *B. sorokiniana* may occur as long as there is a suitable temperature and humidity. In the method of the present disclosure, the temperature is controlled in an incubator, and the plastic cover is used to maintain the moisture and the temperature and humidity required for the induction of leaf blight can be satisfied. Therefore, the identification method of the present disclosure can be carried out all year round.

2. Shorter Time

The entire operation process can be completed in only 20 days from seed germination to the end of identification and can be performed more than 15 times a year. Compared with the methods that are carried out once a year in the field, the identification time is greatly shortened and the identification efficiency is improved. Compared with the field identification methods, the cross breeding can be carried out one year in advance. Therefore, rapid identification is the most prominent innovation and beneficial effect for the method of the present disclosure.

3. Stable Results

The present disclosure is carried out in a controlled indoor environment, and conditions such as temperature and humidity are easy to control. Compared with the open environment in the field, in which unstable identification results for different cultivars are resulted from the changes of black point incidence in different years and different locations, the identification results from the method of the present disclosure are more stable.

4. Saved Manpower and Material Resources

Compared with the tedious steps in field identification such as planting, preventing contamination, inoculation, bagging, harvesting, threshing, investigation, etc. the method of the present disclosure needs only the procedures of seedlings cultivation, identification by pathogen inoculation, moisture maintaining, and investigation, thus saving a lot of manpower and material resources.

In summary, the technical scheme of the present disclosure uses the percentage of the diseased leaf area of leaf blight caused by *B. sorokiniana* at the seedling stage to calculate the black point incidence, which allows for quick identification of resistance of wheat to black point disease caused by *B. sorokiniana*, thus saving valuable scientific research time and a lot of manpower and material resources, and better consistency of the identification results is achieved. Therefore, the method of the present disclosure used for the identification of resistance of wheat to the black point disease caused by *B. sorokiniana* can accurately and efficiently screen resistant and susceptible cultivars, allowing for phenotypic identification of genetic segregation populations and facilitating the inheritance of wheat resistance to black point disease caused by *B. sorokiniana*, the researches on gene/QTL mapping and molecular marker development. It is conducive to advancing genetic research and disease-resistant breeding of wheat against the black point disease caused by *B. sorokiniana*.

The percentage of the disease leaf area of leaf blight under the conditions of different moisture maintaining time and *B. sorokiniana* conidia concentration in the present disclosure is shown in Table 1 in detail.

The results of the regression analysis of the black point incidence and percentage of diseased leaf area of leaf blight for 54 wheat cultivars/lines inoculated with *B. sorokiniana* in the present disclosure are shown in FIG. 1 in detail.

DESCRIPTION OF THE DRAWINGS

In FIG. 1, the percentage of black point incidence and the percentage of leaf blights shows significantly negative correlation, the correlation coefficient (r) is −0.95, the regression equation of the two is y=−1.0037x+66.1360, and the coefficient of determination ($r^2$) is 0.90, y and x in the equation are the percentage of black point incidence and the diseased area, respectively.

FIG. 2 shows the results for the regression analysis of the black point incidence and the black point incidence by the

TABLE 1

Figure 1:
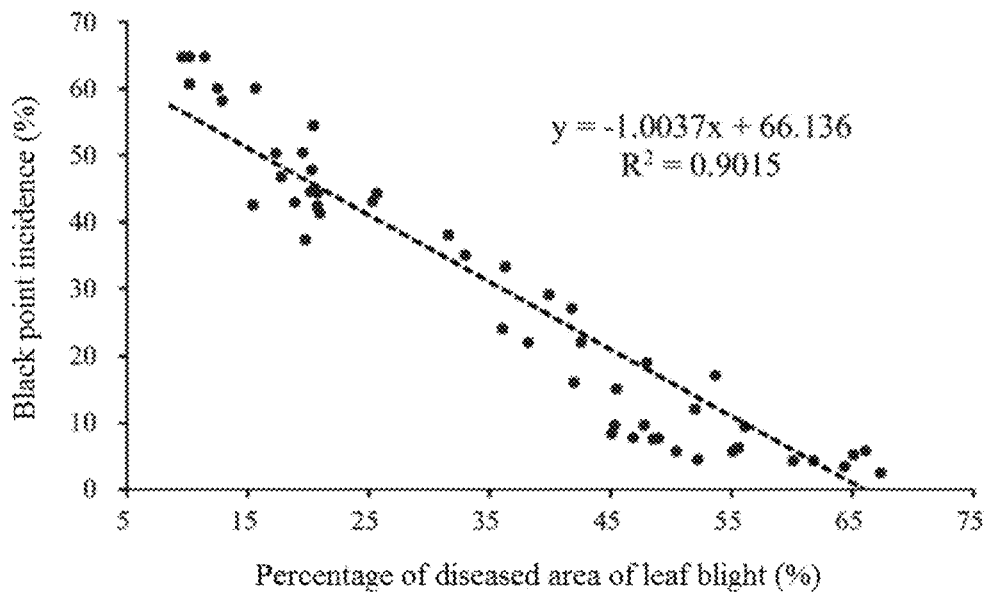
FIG. 1 shows the results for regression analysis of the black point incidence and percentage of diseased leaf area for 54 wheat cultivars/lines inoculated with *B. sorokiniana* in the present disclosure.

Diseased leaf area of leaf blight under different moisture maintaining time and concentration of *B. sorokiniana* conidia suspension

| Wheat strain | Moisture maintaining time | Concentration of conidia suspension (conidia/mL) | | | | | |
| --- | --- | --- | --- | --- | --- | --- | --- |
| | | $1 \times 10^4$ | $5 \times 10^4$ | $1 \times 10^5$ | $5 \times 10^5$ | $1 \times 10^6$ | CK |
| Zheng 2062 | 0 d | 0.0 D | 0.0 C | 0.0 C | 0.0 C | 0.0 C | 0.0 |
| | 2 d | 0.1 D | 0.5 C | 1.4 C | 2.5 C | 3.4 C | 0.0 |
| | 3 d | 0.9 C | 1.1 C | 2.0 C | 3.3 C | 4.2 C | 0.0 |
| | 4 d | 1.1 C | 1.6 C | 3.6 C | 4.6 C | 4.9 C | 0.0 |
| | 5 d | 1.4 BC | 4.4 B | 10.4 B | 11.4 B | 12.9 B | 0.0 |
| | 10 d | 2.1 AB | 8.1 A | 15.1 AB | 18.1 A | 21.4 A | 0.5 |
| | 12 d | 2.7 A | 10.1 A | 18.1 A | 21.1 A | 25.1 A | 0.8 |
| | average | 1.2 | 3.5 | 7.3 | 8.7 | 10.3 | 0.2 |
| 11-253 (LWX) | 0 d | 0.0 D | 0.0 C | 0.0 D | 0.0 C | 0.0 C | 0.0 |
| | 2 d | 0.6 D | 1.6 C | 3.6 CD | 4.4 C | 4.9 C | 0.0 |
| | 4 d | 1.7 D | 2.5 C | 5.7 CD | 6.9 C | 7.1 C | 0.0 |
| | 6 d | 3.6 D | 7.1 C | 25.6 C | 29.6 B | 31.2 B | 0.0 |
| | 8 d | 15.1 C | 21.1 B | 60.1 B | 67.1 A | 70.4 A | 0.0 |
| | 10 d | 25.4 B | 28.4 B | 75.4 AB | 81.4 A | 86.4 A | 0.0 |
| | 12 d | 34.4 A | 41.4 A | 85.4 A | 89.4 A | 91.4 A | 0.2 |
| | average | 11.5 | 14.6 | 36.5 | 39.8 | 41.6 | 0.0 |

Note:
Zheng 2062 was obtained from Henan Academy of Agricultural Sciences, and 11-253 (LWX) was obtained from Henan Agricultural University.
number of days in the table represents the days after inoculation treatment as described in step d) in the present disclosure (i.e. the number of days for the suspension of *Bipolaris sorokiniana* conidia to be shaken and sprayed on the leaves of the wheat growing to a one-leaf-one-shoot stage, then the wheat was covered with a transparent plastic cover and cultured in the incubator), the identification result is expressed as the percentage of diseased leaf area, and data within a column followed by different letters differ significantly at P < 0.01.

After inoculation treatment by conidia suspension with different concentrations, the diseased leaf area increases with increasing concentration of the conidia suspension. When the concentration of the conidia suspension is higher than $1 \times 10^5$ conidia/mL, the increase in diseased area becomes mild, thus the concentration of $1 \times 10^5$/mL of *B. sorokiniana* conidia suspension are chosen as the concentration used for identification in the present disclosure.

The average diseased leaf area increased as the moisture maintaining time increased. At 10 days after the treatment, the diseased area increased dramatically and there was no significant difference in comparison to the treatment after 12 days. Thus, a time period of 10 days was used as the time required for resistance identification.

Based on the diseased leaf area of leaf blight, the concentration of $1 \times 10^5$ conidia/mL and 10 days of inoculation treatment were selected as conditions for identifying the resistance of wheat to black point disease in the present disclosure.

field identification methods for 54 wheat cultivars or lines infected by *B. sorokiniana* in the present disclosure.

Figure 2:
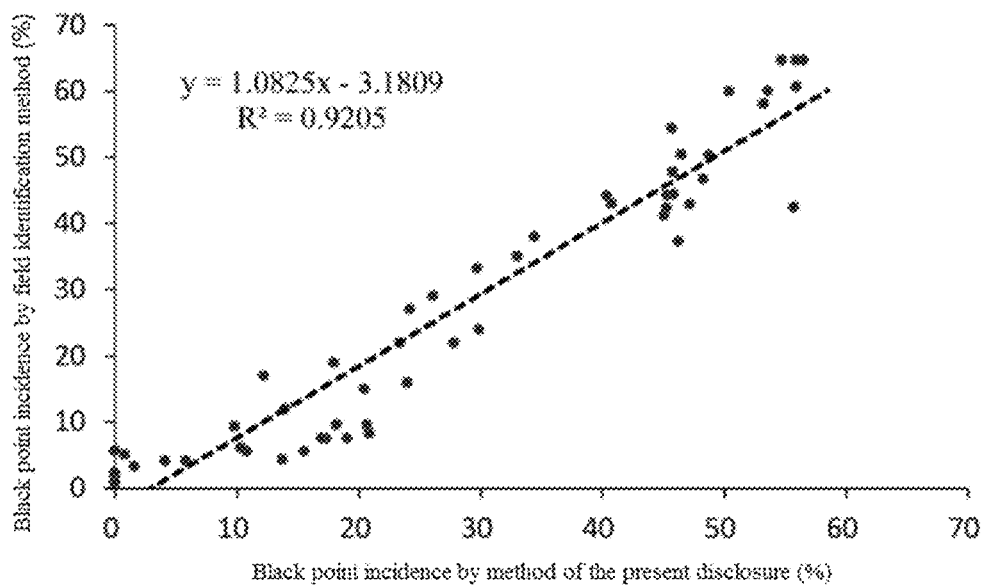

In FIG. 2, the black point incidence calculated in the present disclosure has a significantly positive correlation with the black point incidence identified in the field condition, and the correlation coefficient (r) is 0.96.

Figure 3:
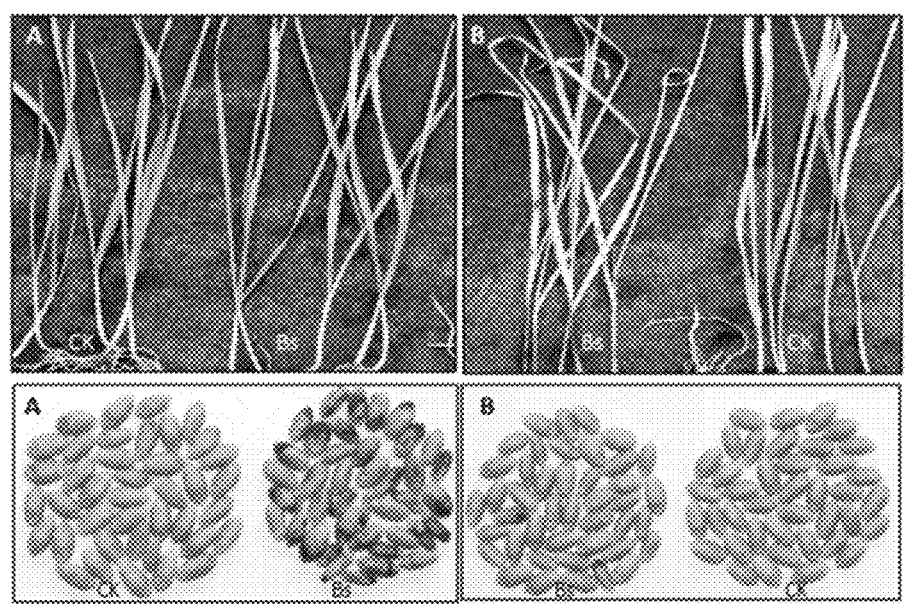

FIG. 3 shows the typical wheat lines screened by the technical scheme of the present disclosure, which are resistant or susceptible to black point disease caused by *B. sorokiniana*.

In FIG. 3, the upper part shows the status of the spots of the leaf blight after inoculation with *B. sorokiniana*; the lower part shows the status of black point disease after inoculation with *B. sorokiniana*. A is the wheat line of Zhumai 6097, which is susceptible to black point disease; B is the wheat line of Shannong 530070, which is resistant to black point disease; CK is a control in which distilled water is sprayed, Bs represents the lines that is sprayed with conidia suspension of *B. sorokiniana*.

DETAILED DESCRIPTION OF THE EMBODIMENTS

The present disclosure will be further described below in conjunction with the embodiments, but these embodiments are not intended to limit the protection scope of the present disclosure.

Example 1

In the winter of 2016, the method of the present disclosure for rapid indoor identification of the resistance of wheat to black point disease caused by *Bipolaris sorokiniana* was used to identify the resistance of 54 wheat cultivars or lines harvested in Xingyang to black point disease. The detailed steps are described as follows.

Surface sterilization of wheat seeds: healthy and full wheat seeds from 54 wheat cultivars or lines were selected and soaked in 70% (volume ratio) alcohol for 2 minutes, then the seeds were rinsed with sterilized distilled water for 3 times, and shaken gently for 5 seconds each time after adding distilled water, so that the alcohol remaining on the surface of the seeds was fully dissolved in the water to prevent the alcohol from inhibiting the germination of wheat seeds;

Wheat seedling cultivation: the wheat seeds that had been surface-sterilized in step a) were placed in Petri dishes with a diameter of 9 cm. To each Petri dish were added 2 layers of sterilized filter paper and 4 mL of sterilized distilled water in advance. Five wheat cultivars or lines were placed in each Petri dish, 15 seeds per cultivar/line. Then the Petri dishes were placed in a 25° C. incubator for 3 days in the dark. After 3 days, the wheat seeds with inconsistent germination potential were picked out, 10 mL of sterilized distilled water was supplemented to each Petri dish, and the cover of the Petri dishes were removed. The temperature and light cycle in the incubator was alternated between "25° C., light, 11 hours" and "21° C., dark, 13 hours", and then 7-day culturing was continued.

Preparation of suspensions of *B. sorokiniana* conidia: the *B. sorokiniana* stored in a 4° C. refrigerator ready for use was cut into 0.3 cm$^2$ pieces and inoculated into potato dextrose agar (PDA) medium, and the *B. sorokiniana* were cultured in the dark at 25° C. for 7 days. The conidia production was observed. If the color of the colony was gray, it indicated that the number of conidia was too small. The sealing film of the Petri dishes needed to be removed for further culture. The Petri dishes were taken out when the color of the colonies became deep black and a large number of conidia were produced. The conidia were gently scraped off the Petri dishes with a sterilized glass slide. The Petri dishes were rinsed 3 times with sterilized distilled water, and mycelial fragment were filtered with a four-layer gauze to obtain the suspension of *B. sorokiniana* conidia, and the concentration of conidia suspension was measured by means of a hemocytometer and adjusted to a spore concentration of 1×10$^5$/mL;

Inoculation and identification: the suspension of *B. sorokiniana* conidia prepared in step c) was shaken and sprayed on the wheat leaves growing to one-leaf-one-shoot stage in step b), and the wheat leaves were covered with a transparent plastic cover and then placed in an incubator, cultured in the dark at 25° C. for 24 hours. After 24 hours, the temperature and light cycle in the incubator was alternated between "25° C., light, 11 hours" and "25° C., dark, 13 hours", and cultured for another 9 days. 3 mL of sterilized distilled water was sprayed evenly into the cover by using a hand sprayer, twice a day in the morning and in the evening to maintain a high humidity required for infection of *B. sorokiniana* and for development of leaf blight;

Recording of identification results: the percentage of the diseased leaf area in the total leaf area of the first leaf of the wheat seedling in step d) was recorded on the 10$^{th}$ day of inoculation, and the percentage of diseased leaf area was obtained;

Calculation of Black Point Incidence of the Wheat:

Calculate the percentage of black point grain (namely the black point incidence) from the identified diseased leaf area percentage by using the equation y=−1.0037x+66.1360. In the equation, y and x are the black point incidence and the percentage of diseased leaf area, respectively.

g) Evaluation of resistance to black point disease:

The resistance of wheat to black point disease caused by *B. sorokiniana* was evaluated based on the black point incidence calculated in step f) (the method for evaluating the resistance of wheat to black point disease comprises recording as I if there are no diseased grains, which is considered to be immune; recording as HR if the black point incidence is 0.1% to 1.9%, which is considered to be highly resistance; recording as R if the black point incidence is from 2.0% to 4.9%, which is considered to be resistant; recording as SS if the black point incidence is from 5.0% to 14.9%, which is considered to be of slightly susceptible; recording as MS if the black point incidence is from 15.0% to 30.0%, which is considered to be moderately susceptible; and recording as HS if the black point incidence is greater than 30%, which is considered to be highly susceptible).

The identification results for 54 wheat cultivars or lines are shown in Table 2 and FIG. 1 in detail. It can be seen from FIG. 1 that the larger the diseased leaf area of leaf blight caused by *B. sorokiniana* at the seedling stage of wheat, the lower the black point incidence caused by *B. sorokiniana* at the field filling stage is. That is, there is a significantly negative correlation between the area of the diseased leaf area of the leaf blight at the seedling stage and the black point incidence, the correlation coefficient reached −0.95. Through regression analysis, the coefficient of determination was 0.90. The comparison of the resistance evaluation of 54 wheat strains using the method of the present disclosure to the field identification results for inoculation showed that 50 in 54 of wheat cultivars or lines presented consistent identification results, and resistance identification results for only 4 lines had inconsistent results (see Table 2). The black point incidence calculated based on the diseased leaf area of leaf blight was significantly correlated with the actual black point incidence identified in the field, with a correlation coefficient being 0.96. The above results indicate that the technical scheme of the present disclosure can better evaluate the resistance of wheat to black point disease caused by *B. sorokiniana*.

TABLE 2

Comparison of results for field inoculation identification to results for resistance identification of the present disclosure for 54 wheat cultivars/lines harvested in 2016

| No. | Wheat cultivar/lines | Black point incidence by field identification method (%) | Resistance evaluation by field identification method | Black point incidence calculated by method of the present disclosure (%) | Resistance evaluation by method of the present disclosure |
|---|---|---|---|---|---|
| 1 | Guomai 2 | 0.9 | HR | 0.1 | HR |
| 2 | Wenmai 10 | 2.0 | R | 0.2 | HR |
| 3 | Shannong 530070 | 2.4 | R | 0.0 | I |
| 4 | SN4143 | 3.3 | R | 1.6 | HR |
| 5 | 11-253 | 4.2 | R | 4.1 | R |
| 6 | L661 (LPG) | 4.2 | R | 5.8 | SS |
| 7 | Xinong 9871-1 | 4.4 | R | 13.7 | SS |
| 8 | Wenmai 8 | 4.9 | R | 0.1 | HR |
| 9 | 481/274 | 5.1 | SS | 0.8 | HR |
| 10 | Huixianhong | 5.6 | SS | 10.8 | SS |
| 11 | 04ZP16 | 5.6 | SS | 15.5 | MS |
| 12 | 11-696 | 5.7 | SS | 0.0 | I |
| 13 | 11-269 | 6.2 | SS | 10.3 | SS |
| 14 | 11-285 | 7.5 | SS | 17.4 | MS |
| 15 | Bima 1 | 7.6 | SS | 17.0 | MS |
| 16 | Shi 98-7136 | 7.6 | SS | 19.1 | MS |
| 17 | SP1777-6-8 | 8.3 | SS | 20.9 | MS |
| 18 | Wangshuibai | 9.4 | SS | 9.8 | SS |
| 19 | Sumai 3 | 9.6 | SS | 18.2 | MS |
| 20 | 92R137 | 9.6 | SS | 20.7 | MS |
| 21 | 15YD55 | 12.0 | SS | 13.9 | SS |
| 22 | GM15 | 15.0 | MS | 20.5 | MS |
| 23 | 15YD77 | 16.0 | MS | 24.0 | MS |
| 24 | 15YD14 | 17.0 | MS | 12.2 | SS |
| 25 | 15YD56 | 19.0 | MS | 18.0 | MS |
| 26 | PH691 | 22.0 | MS | 27.8 | MS |
| 27 | 15YQ24 | 22.0 | MS | 23.4 | MS |
| 28 | Xuke 316 | 24.0 | MS | 29.9 | MS |
| 29 | 15YQ39 | 27.0 | MS | 24.2 | MS |
| 30 | 15YQ41 | 29.0 | MS | 26.1 | MS |
| 31 | 11-239 | 33.2 | HS | 29.7 | MS |
| 32 | 15YQ33 | 35.0 | HS | 33.0 | HS |
| 33 | Xumai 9169 | 37.3 | HS | 46.3 | HS |
| 34 | 15YQ29 | 38.0 | HS | 34.4 | HS |
| 35 | Yumai 47 | 41.2 | HS | 45.1 | HS |
| 36 | 11YC173 | 42.4 | HS | 45.3 | HS |
| 37 | Zheng 2062 | 42.5 | HS | 55.7 | HS |
| 38 | Wanyuanbai 1 | 42.9 | HS | 47.2 | HS |
| 39 | Jinan 31 | 43.0 | HS | 40.7 | HS |
| 40 | Xinaizao 818 | 44.2 | HS | 40.3 | HS |
| 41 | Danti (NIU) | 44.3 | HS | 45.3 | HS |
| 42 | Aifeng 66 | 44.4 | HS | 45.9 | HS |
| 43 | YN177 | 46.7 | HS | 48.3 | HS |
| 44 | Helandazi | 47.8 | HS | 45.8 | HS |
| 45 | Chinese Spring | 50.3 | HS | 48.8 | HS |
| 46 | Tunmai 127 | 50.4 | HS | 46.5 | HS |
| 47 | He 0927 | 54.4 | HS | 45.7 | HS |
| 48 | Zhumai 6097 | 58.1 | HS | 53.2 | HS |
| 49 | PZSCL6 | 60.0 | HS | 50.4 | HS |
| 50 | Bainong 107 | 60.0 | HS | 53.6 | HS |
| 51 | 10M24 | 60.7 | HS | 55.9 | HS |
| 52 | 11-229 | 64.7 | HS | 54.7 | HS |
| 53 | Jicheng 2 | 64.7 | HS | 56.5 | HS |
| 54 | Yuaniia 69 | 64.7 | HS | 55.9 | HS |

Note:
The diseased leaf area of leaf blight is the identification result for the indoor inoculation with *B. sorokiniana* in the winter of 2016 in the present disclosure. The black point incidence is the identification result for the field inoculation with *B. sorokiniana* during the grain filling stage in 2016. The method for field identification of resistance to black point disease referred to the Chinese patent (ZL 2015105396457).
In the black point resistance evaluation: I represents immune (black point incidence is 0.0%), HR represents highly resistant (0.1-1.9%), R represents resistant (2.0-4.9%), SS represents slightly susceptible (5.0-14.9%), MS represents moderately susceptible (15.0-30.0%), HS represents highly susceptible (black point incidence >30%). The identification result is that the immune, highly resistant and resistant are considered resistant cultivars/lines, while the slightly susceptible, the moderately susceptible strains and highly susceptible are considered susceptible cultivars/lines.

Example 2

Ten (10) disease-resistant wheat cultivars/lines were identified for 3 consecutive years by using the method for quickly identifying wheat resistance to black point disease caused by B. sorokiniana in the present disclosure, and the results were compared with the field identification results.

The detailed steps are as follows

Surface sterilization of wheat seeds: healthy and full wheat seeds were selected and soaked in 70% (volume ratio) alcohol for 2 minutes, then the seeds were rinsed with sterilized distilled water for 3 times, and shaken gently for 5 seconds each time after adding distilled water, so that the alcohol remaining on the surface of the seeds was fully dissolved in the water to prevent the alcohol from inhibiting the germination of wheat seeds;

Wheat seedling cultivation: the wheat seeds that had been surface-sterilized in step a) were placed in Petri dishes with a diameter of 9 cm. Each Petri dish was added 2 layers of sterilized filter paper and 4 mL of sterilized distilled water in advance. Five wheat cultivars or lines were placed in the each Petri dish, 15 grains per cultivar or line. Then the Petri dishes were placed in a 25° C. incubator for 3 days in the dark. After 3 days, the wheat seeds with inconsistent germination potential were picked out, 10 mL of sterilized distilled water was supplemented to each Petri dish, and the cover of the Petri dishes were removed. The temperature and light cycle in the incubator was alternated between "25° C., light, 11 hours" and "21° C., dark, 13 hours", and then 7-day culturing was continued.

c) Preparation of suspension of B. sorokiniana conidia: the B. sorokiniana stored in a 4° C. refrigerator ready for use was cut into 0.3 cm² pieces and inoculated into potato dextrose agar (PDA) medium, and the B. sorokiniana conidia were cultured in the dark at 25° C. for 7 days. The conidia production was observed. If the color of the colony was gray, it indicated that the number of conidia was too small. The sealing film over the Petri dishes needed to be removed for further culture. The Petri dishes were taken out when the color of the colonies became deep black and a large number of conidia were produced. The conidia were gently scraped off the Petri dishes with a sterilized glass slide. The Petri dishes were rinsed 3 times with sterilized distilled water, and mycelial fragment were filtered with a four-layer gauze to obtain the suspension of B. sorokiniana conidia, and the concentration of conidia suspension was measured by means of a hemocytometer and adjusted to a conidia concentration of $1\times10^5$/mL;

d) Inoculation and identification: the suspension of B. sorokiniana conidia prepared in step c) was shaken and sprayed on the wheat leaves growing to one-leaf-one-shoot stage in step b), and the wheat leaves were covered with a transparent plastic cover and then placed in an incubator, cultured in the dark at 25° C. for 24 hours. After 24 hours, the temperature and light cycle in the incubator was alternated between "25° C., light, 11 hours" and "25° C., dark, 13 hours", and cultured for another for 9 days. 3 mL of sterilized distilled water was sprayed evenly into the cover by using a hand sprayer, twice a day in the morning and in the evening to maintain a high humidity required for infection of B. sorokiniana and for development of leaf blight;

e) Recording of identification results: the percentage of the diseased leaf area in the total leaf area of the first leaf of the wheat seedling in step d) was recorded on the $10^{th}$ day of inoculation, and the percentage of diseased leaf area was obtained;

f) Calculation of black point incidence of the wheat:

Calculate the percentage of black point grain (namely the black point incidence) from the identified percentage of diseased leaf area by using the equation $y=-1.0037x+66.1360$. In the equation, y and x are the black point incidence and the percentage of diseased leaf area, respectively.

g) Evaluation of resistance to disease:

The resistance of wheat to black point disease caused by B. sorokiniana was evaluated based on the black point incidence calculated in step f) (the method for evaluating the resistance of wheat to black point disease comprises recording as I if there are no diseased grains, which is considered to be immune; recording as HR if the black point incidence is from 0.1% to 1.9%, which is considered to be highly resistant; recording as R if the black point incidence is from 2.0% to 4.9%, which is considered to be resistant; recording as SS if the black point incidence is from 5.0% to 14.9%, which is considered to be of slightly susceptible; recording as MS if the black point incidence is from 15.0% to 30.0%, which is considered to be moderately susceptible; and recording as HS if the black point incidence is greater than 30%, which is considered to be highly susceptible).

In the present disclosure, 10 wheat cultivars/lines were identified for the resistance to black point disease caused by B. sorokiniana in three consecutive years and the results were compared with the results for the field identification, the comparison results are shown in Table 3 and FIG. 3. The results in Table 3 show that during the three years, there is consistency among the results for resistance to the black point disease caused by B. sorokiniana for 10 cultivars/lines identified by the method of the present disclosure. However, under field conditions, due to the effect of the meteorological factors such as temperature, humidity, sunshine length etc. the resistance evaluation of 9 in 10 cultivars or lines are inconsistent from year to year. For example, the black point incidence for Guomai 2 varies from 0.9% to 9.1% in three years, and the resistance evaluation results are R, HR, and SS, respectively. This result will lead to deviation in the resistance evaluation for the same wheat cultivar/line. In contrast, the use of the identification method of the present disclosure gives consistency between the identification results for three years, which ensures the consistency of the resistance evaluation.

TABLE 3

Comparison of the results for identification of wheat resistance to black point disease caused by B. sorokiniana by method of the present disclosure with the results for field identification for three consecutive years

| Wheat cultivars/lines | Black point incidence by method of the present disclosure (%) | | | Identification result by method of the present disclosure | | |
|---|---|---|---|---|---|---|
|  | 2016 | 2017 | 2018 | 2016 | 2017 | 2018 |
| Wenmai 10 | 0.1 | 0.1 | 1.1 | HR | HR | HR |
| 481/274 | 1.6 | 0.2 | 0.4 | HR | HR | HR |
| 11-253 | 4.0 | 0.0 | 3.5 | R | I | R |
| 11-696 | 4.6 | 0.0 | 3.0 | R | I | R |

TABLE 3-continued

Comparison of the results for identification of wheat resistance to black point disease caused by B. sorokiniana by method of the present disclosure with the results for field identification for three consecutive years

| | | | | | | |
|---|---|---|---|---|---|---|
| SN4143 | 8.3 | 5.8 | 5.0 | SS | SS | SS |
| Shannong 530070 | 4.9 | 0.0 | 3.0 | R | I | R |
| L661 (LPG) | 10.3 | 13.7 | 5.3 | SS | SS | SS |
| Wenmai 8 | 1.5 | 0.1 | 0.0 | HR | HR | HR |
| Xinong 9871-1 | 2.5 | 0.8 | 0.0 | R | HR | HR |
| Guomai 2 | 4.1 | 0.0 | 1.9 | R | I | HR |

| Wheat cultivars/lines | Black point incidence by Field identification | | | Field identification results | | |
|---|---|---|---|---|---|---|
| | 2016 | 2017 | 2018 | 2016 | 2017 | 2018 |
| Wenmai 10 | 1.9 | 2.0 | 2.5 | HR | R | R |
| 481/274 | 4.4 | 5.1 | 4.8 | R | SS | R |
| 11-253 | 4.4 | 4.2 | 5.4 | R | R | SS |
| 11-696 | 3.5 | 5.7 | 6.1 | R | SS | SS |
| SN4143 | 6.8 | 3.3 | 7.4 | SS | R | SS |
| Shannong 530070 | 1.5 | 2.4 | 7.6 | HR | R | SS |
| L661 (LPG) | 9.1 | 4.2 | 8.7 | SS | R | SS |
| Wenmai 8 | 5.0 | 4.9 | 8.8 | SS | R | SS |
| Xinong 9871-1 | 4.4 | 4.4 | 8.9 | R | R | SS |
| Guomai 2 | 4.5 | 0.9 | 9.1 | R | HR | SS |

Note:
The three-year field resistance identification test was completed in Xingyang Breeding Field (Yulong Town, Xingyang City, Henan Province, China), and the method for field identification of resistance to black point disease referred to the Chinese invention patent (ZL 2015105396457).
In the resistance evaluation, I, HR, R, and SS represent immune, highly resistant, resistant, and slightly susceptible, respectively.

When identified using the method of the present disclosure, there is consistent evaluation of resistance of 10 strains to black point disease caused by B. sorokiniana during 3 years. However, under field conditions, 9 of 10 strains have inconsistent results for resistance evaluation between two years.

Example 3

By using the method for rapid indoor identification of the resistance of wheat to the black point disease caused by B. sorokiniana, two of ten advanced lines from the $F_4$ and $F_5$ were identified to be resistant lines in March 2018. Crossing was conducted in April 2018 in the field, and breeding efficiency is improved compared with field identification method. Cross breeding may be carried out one year earlier. The detailed steps are described as follows.

Surface sterilization of wheat seeds: healthy and full wheat seeds from 10 advanced $F_4$ and $F_5$ wheat lines were selected and soaked in 70% (volume ratio) alcohol for 2 minutes, then the seeds were rinsed with sterilized distilled water for 3 times, and shaken gently for 5 seconds each time after adding distilled water, so that the alcohol remaining on the surface of the seeds was fully dissolved in the water to prevent the alcohol from inhibiting the germination of wheat seeds;

Wheat seedling cultivation: the wheat seeds that had been surface-sterilized in step a) were placed in Petri dishes with a diameter of 9 cm. Each Petri dish was added 2 layers of sterilized filter paper and 4 mL of sterilized distilled water in advance. Five wheat lines were placed in each Petri dish, 15 grains per lines. Then the Petri dishes were placed in a 25° C. incubator for 3 days in the dark. After 3 days, the wheat seeds with inconsistent germination potential were picked out, 10 mL of sterilized distilled water was supplemented to each Petri dish, and the cover of the Petri dishes were removed. The temperature and light cycle in the incubator was alternated between "25° C., light, 11 hours" and "21° C., dark, 13 hours", and then 7-day culturing was continued.

Preparation of suspension of B. sorokiniana conidia: the B. sorokiniana stored in a 4° C. refrigerator ready for use was cut into 0.3 cm² pieces and inoculated into potato dextrose agar (PDA) medium, and B. sorokiniana were cultured in the dark at 25° C. for 7 days. The conidia production was observed. If the color of the colony was gray, it indicated that the number of conidia was too small. The sealing film over the Petri dishes needed to be removed for further culture. The Petri dishes were taken out when the color of the colonies became deep black and a large number of conidia were produced. The conidia were gently scraped off the Petri dishes with a sterilized glass slide, the Petri dishes was rinsed 3 times with sterilized distilled water, and mycelial fragment were filtered with a four-layer gauze to obtain the suspension of B. sorokiniana conidia, and the concentration of conidia suspension was measured by means of a hemocytometer and adjusted to a conidia concentration of $1 \times 10^5$/mL;

Inoculation and identification: the suspension of B. sorokiniana conidia prepared in step c) was shaken and Tween 20 in amount of 0.02% by volume with respect to the suspension of B. sorokiniana was added, and sprayed with a hand sprayer on the wheat leaves growing to one-leaf-one-shoot stage in step b), and the wheat leaves were covered with a transparent plastic cover and then placed in an incubator, cultured in the dark at 25° C. for 24 hours. After 24 hours, the temperature and light cycle in the incubator was alternated between "25° C., light, 11 hours" and "25° C., dark, 13 hours", and cultured for another 9 days. 3 mL of sterilized distilled water was sprayed evenly into the cover by using a watering can, twice a day in the morning and in the evening to maintain a high humidity required for *B. sorokiniana* infection and development of leaf blight;

Recording of identification results: the percentage of the diseased leaf area in the total leaf area of the first leaf of the wheat seedling in step d) was recorded on the $10^{th}$ day of inoculation, and the percentage of diseased leaf area was obtained;

Calculation of Black Point Incidence of the Wheat:

Calculate the percentage of black point grains (namely the black point incidence), from the identified percentage of diseased leaf area by using the equation $y=-1.0037x+66.1360$. In the equation, y and x are the black point incidence and the percentage of diseased leaf area, respectively;

the black point incidence is from 15.0% to 30.0%, which is considered to be moderately susceptible; and recording as HS if the black point incidence is greater than 30%, which is considered to be highly susceptible).

In March 2018, ten advanced lines were identified in an indoor, controlled environment for black point disease, and the results are shown in Table 4. According to the results of the indoor identification, two lines resistant to black point disease were screened among the 10 advanced lines (17YH24 and 17YQ13). These two lines were crossed with high-yielding wheat cultivars in April 2018. If identified in the field, the identification had to be conducted at the end of April and the crossing could be done till the year of 2019. Therefore, by adopting the method of the present disclosure, the breeding process of wheat resistant to black point disease can be preceded by one year.

TABLE 4

Identification results for the resistance of ten advanced $F_4$ and $F_5$ wheat lines to black point disease caused by *B. sorokiniana* by using the method of the present disclosure

| No. | Combination | Generation | Identification time | Identification result by the method of the present disclosure | Crossing time | Field identification time |
| --- | --- | --- | --- | --- | --- | --- |
| 17YH22 | Zhoumai $22^2$/Zhengfeng 99745 | $F_4$ | March 2018 | SS | | April-June 2018 |
| 17YH23 | Zhoumai $22^2$/Zhengfeng 99745 | $F_4$ | March 2018 | SS | | April-June 2018 |
| 17YH24 | Shengnong $2^2$/Zhengfeng 99745 | $F_4$ | March 2018 | R | April 2018 | April-June 2018 |
| 17YH25 | Shengnong $2^2$/Zhengfeng 99745 | $F_4$ | March 2018 | SS | | April-June 2018 |
| 17YH26 | Shengnong $2^2$/Zhengfeng 99745 | $F_4$ | March 2018 | HS | | April-June 2018 |
| 17YH27 | Shengnong $2^2$/Zhengfeng 99745 | $F_4$ | March 2018 | HS | | April-June 2018 |
| 17YQ13 | Shengnong 2/Shannong 4143 | $F_5$ | March 2018 | R | April 2018 | April-June 2018 |
| 17YQ14 | Shengnong 2/Shannong 4143 | $F_5$ | March 2018 | MS | | April-June 2018 |
| 17YQ15 | Zhoumai 22/Shannong 4143 | $F_5$ | March 2018 | MS | | April-June 2018 |
| 17YQ16 | Zhoumai 22/Shannong 4143 | $F_5$ | March 2018 | SS | | April-June 2018 |

Note:
In the resistance evaluation, I, HR, R, SS, MS, HS represent immune, highly resistant, resistant, slightly susceptible, moderately susceptible, and highly susceptible.
The texts in bold (row 17YH24 and row 17YQ13) represent two resistant advanced lines screened for crossing. The susceptible lines are the eliminated breeding materials which were no longer used for cross-breeding.

g) Evaluation of resistance to disease:

The resistance of wheat to black point disease caused by *B. sorokiniana* was evaluated based on the black point incidence calculated in step f) (the method for evaluating the resistance of wheat to black point disease comprises recording as I if there are no diseased grains, which is considered to be immune; recording as HR if the black point incidence is from 0.1% to 1.9%, which is considered highly resistant; recording as R if the black point incidence is from 2.0% to 4.9%, which is considered to be resistant; recording as SS if the black point rate is from 5.0% to 14.9%, which is considered to be of slightly susceptible; recording as MS if Example 4

By using the method of the present disclosure for rapid indoor identification of wheat resistance to black point disease caused by *B. sorokiniana*, 105 wheat cultivars or lines that were planted on a large scale or under pilot production were identified in an indoor, controlled environment on March 2018, and 3 resistant lines were screened, saving more than 50% of manpower and material resources. The detailed steps are described as follows.

Surface sterilization of wheat seeds: healthy and full seeds from 105 wheat strains were selected and soaked in 70%

(volume ratio) alcohol for 2 minutes, then the seeds were rinsed with sterilized distilled water for 3 times, and shaken gently for 5 seconds each time after adding distilled water, so that the alcohol remaining on the surface of the seeds was fully dissolved in the water to prevent the alcohol from inhibiting the germination of wheat seeds;

Wheat seedling cultivation: the wheat seeds that had been surface-sterilized in step a) were placed in Petri dishes with a diameter of 9 cm. Each Petri dish was added 2 layers of sterilized filter paper and 4 mL of sterilized distilled water in advance. Five wheat cultivars/lines were placed in each Petri dish, 15 grains per cultivar/line. Then the Petri dishes were placed in a 25° C. incubator for 3 days in the dark. After 3 days, the wheat seeds with inconsistent germination potential were picked out, 10 mL of sterilized distilled water was supplemented to each Petri dish, and the cover of the Petri dishes were removed. The temperature and light cycle in the incubator was alternated between "25° C., light, 11 hours" and "21° C., dark, 13 hours", and then a 7-day culturing was continued.

Preparation of suspension of *B. sorokiniana* conidia: the *B. sorokiniana* stored in a 4° C. refrigerator ready for use was cut into 0.3 $cm^2$ pieces and inoculated into potato dextrose agar (PDA) medium, and *B. sorokiniana* were cultured in the dark at 25° C. for 7 days. The conidia production was observed. If the color of the colony was gray, it indicated that the number of conidia was too small. The sealing film over the Petri dishes needed to be removed for further culture. The Petri dishes were taken out when the color of the colonies became deep black and a large number of conidia were produced. The conidia were gently scraped off the Petri dishes with a sterilized glass slide, the Petri dishes was rinsed 3 times with sterilized distilled water, and mycelial fragment were filtered with a four-layer gauze to obtain the suspension of *B. sorokiniana* conidia, and the concentration of conidia suspension was measured by means of a hemocytometer and adjusted to a spore concentration of $1 \times 10^5$/mL;

Inoculation and identification: the suspension of *B. sorokiniana* conidia prepared in step c) was shaken and Tween 20 in amount of 0.02% by volume with respect to the suspension of *B. sorokiniana* was added, and sprayed with a hand sprayer on the wheat leaves growing to one-leaf-one-shoot stage in step b), and the wheat leaves were covered with a transparent plastic cover and then placed in an incubator, cultured in the dark at 25° C. for 24 hours. After 24 hours, the temperature and light cycle in the incubator was alternated between "25° C., light, 11 hours" and "25° C., dark, 13 hours", and cultured for another 9 days. 3 mL of sterilized distilled water was sprayed evenly into the cover by using a hand sprayer twice a day in the morning and in the evening to maintain a high humidity required for *B. sorokiniana* infection and development of leaf blight;

Recording of identification results: the percentage of the diseased leaf area in the total leaf area of the first leaf of the wheat seedling in step d) was recorded on the $10^{th}$ day of inoculation, and the percentage of diseased leaf area was obtained;

Calculation of Black Point Incidence of the Wheat:

Calculate the percentage of black point grain (namely the black point incidence), from the identified percentage of diseased leaf area by using the equation $y=-1.0037x+66.1360$. In the equation, y and x are the black point incidence and the percentage of diseased leaf area, respectively;

g) Evaluation of resistance to disease:

The resistance of wheat to black point disease caused by *B. sorokiniana* was evaluated based on the black point incidence calculated in step f) (the method for evaluating the resistance of wheat to black point disease comprises: recording as I if there are no diseased grains, which is considered to be immune; recording as HR if the black point incidence is from 0.1% to 1.9%, which is considered highly resistant; recording as R if the black point incidence is from 2.0% to 4.9%, which is considered to be resistant; recording as SS if the black point incidence is from 5.0% to 14.9%, which is considered to be of slightly susceptible; recording as MS if the black point incidence is from 15.0% to 30.0%, which is considered to be moderately susceptible; and recording as HS if the black point incidence is greater than 30%, which is considered to be highly susceptible).

The indoor identification results for 105 wheat cultivars/lines in 2018 are shown in Table 5. Four resistant cultivar/lines were selected from 105 wheat strains. In 2019, the identified resistant cultivar/lines were verified by field inoculation, and 3 wheat cultivar/lines resistant to black point disease were determined. Indoor identification of 105 wheat cultivar/lines took only 20 days, 2 incubators were used, and only one staff is sufficient to complete. If identified in the field, it will require planting at least 105 rows of wheat, a wheat growth season of 200 days, and 2-3 staff to cooperate to complete the field identification. Therefore, the method of the present disclosure for indoor identification of wheat resistance to black point disease caused by *B. sorokiniana* saves at least 50% of manpower and material resources.

TABLE 5

Results for identification of resistance to black point disease caused by *B. sorokiniana* for 105 wheat cultivars or lines by using the method of the present disclosure

| No. | Wheat cultivars/lines | Identification results for the method of the present disclosure | Results for field identification method |
|---|---|---|---|
| 1 | Emai 526 | HS | HS |
| 2 | Guinong 22 | R | R |
| 3 | Nongda 2011 | MS | — |
| 4 | Zhengmai 1860 | MS | — |
| 5 | Zhenmai 3 | MS | — |
| 6 | Taihemai 2 | SS | — |
| 7 | Saidemai 1 | MS | — |
| 8 | Womai 66 | HS | HS |
| 9 | Zhoumai 36 | MS | — |
| 10 | Zhongmai 170 | MS | — |
| 11 | Zhengmai 132 | HS | MS |
| 12 | Fengdecunmai 16 | MS | — |
| 13 | Luomai 956 | HS | MS |
| 14 | Zhumai 305 | HS | HS |
| 15 | Junmai 0821 | HS | HS |
| 16 | Zhongyu 1526 | MS | — |
| 17 | Wenmai 168 | HS | MS |
| 18 | Taixue 518 | MS | — |
| 19 | Chenming 1 | SS | — |
| 20 | Hemai 0666 | SS | — |
| 21 | Dengmai 298 | SS | — |
| 22 | Xiangmai 182 | SS | — |
| 23 | Kemai 1609 | SS | — |
| 24 | Zhengmai 20 | MS | — |
| 25 | Xindifeng 058 | SS | — |
| 26 | Jinmai 23 | HS | HS |
| 27 | Zhongmai 255 | SS | — |
| 28 | Gaoyou 5218 | R | R |
| 29 | Zhengmai 158 | SS | — |
| 30 | Gaoyou 5766 | SS | — |
| 31 | Huaichuan 709 | SS | — |

TABLE 5-continued Results for identification of resistance to black point disease
caused by B. sorokiniana for 105 wheat cultivars or lines
by using the method of the present disclosure

| No. | Wheat cultivars/lines | Identification results for the method of the present disclosure | Results for field identification method |
|---|---|---|---|
| 32 | Zhengyuanmai 5 | SS | — |
| 33 | Xinong 238 | SS | — |
| 34 | Weimai 68 | SS | — |
| 35 | Changyimai 3 | SS | — |
| 36 | Fumai 368 | SS | — |
| 37 | Jinyou 18 | SS | — |
| 38 | Shannong 981 | HS | HS |
| 39 | Bainongyunluo 33 | HS | HS |
| 40 | Luomai 31 | SS | — |
| 41 | Zhengmai 379 | SS | — |
| 42 | Zhoumai 22 | MS | — |
| 43 | Zhoumai 18 | MS | — |
| 44 | Bainong 207 | SS | — |
| 45 | Xun 5366 | MS | — |
| 46 | Yunong 516 | MS | — |
| 47 | Shangdumai 137 | HS | HS |
| 48 | Jiyanmai 10 | HS | HS |
| 49 | Saidemai 8 | HS | MS |
| 50 | Xinong 511 | SS | — |
| 51 | Xinong 585 | SS | — |
| 52 | Ruiquanmai168 | MS | — |
| 53 | Yikemai 5 | MS | — |
| 54 | Ruihua 1426 | SS | — |
| 55 | Yangmai 158 | HS | MS |
| 56 | Zhoumai 32 | HS | MS |
| 57 | Ruihua 055 | SS | — |
| 58 | Xinong 528 | HS | MS |
| 59 | Ruihua 1426 | SS | — |
| 60 | Xinong 239 | SS | — |
| 61 | Nannong 0686 | SS | — |
| 62 | Junmai 802 | HS | HS |
| 63 | Junmai 830 | MS | — |
| 64 | Zhengmai 1867 | HS | HS |
| 65 | Ningmai 13 | SS | — |
| 66 | Ningmai 20 | SS | — |
| 67 | Ningmai 24 | SS | — |
| 68 | Yubao 5018 | MS | — |
| 69 | Yunong 517 | SS | — |
| 70 | Ningmaizi 126 | SS | — |
| 71 | Ningmaizi14213 | R | R |
| 72 | Zhenmai 10 | SS | — |
| 73 | Yangfumai 2166 | SS | — |
| 74 | Ningmaizi 67 | R | SS |
| 75 | Haomai 1 | SS | — |
| 76 | Longmai 28 | SS | — |
| 77 | Yangmai 14 | MS | — |
| 78 | Ningmaizi 119 | SS | — |
| 79 | Xiaoyan 22 | SS | — |
| 80 | Xunong 0029 | SS | — |
| 81 | Huaimai 28 | HS | HS |
| 82 | Annong 1124 | SS | — |
| 83 | Luokang 2 | SS | — |
| 84 | Yumai 18 | SS | — |
| 85 | Yangmai 15 | SS | — |
| 86 | Shannong 20 | SS | — |
| 87 | Gaochanxianfeng | SS | — |
| 88 | Zimai 19 | HS | MS |
| 89 | Yannong 19 | SS | — |
| 90 | Womai 8 | SS | — |
| 91 | Womai 182 | SS | — |
| 92 | Huaimai 28 | SS | — |
| 93 | Huaimai 29 | MS | — |
| 94 | Huaima 35 | MS | — |
| 95 | Weilai 0818 | SS | — |
| 96 | Annong 0711 | SS | — |
| 97 | Annong 1589 | SS | — |
| 98 | Shengxuan No. 5 | SS | — |
| 99 | Shengxuan 6 | SS | — |
| 100 | Tainong 9862 | SS | — |
| 101 | Huaimai 302 | SS | — |
| 102 | Huamai 0772 | SS | — |
| 103 | Wuhan 1 | SS | — |
| 104 | Fengdecunmai 5 | MS | — |
| 105 | Quanmai 29 | MS | — |

Note:
The purpose of this example is to provide typical resistant and susceptible materials for disease resistance breeding and mechanism research on resistance to black point disease. Since field inoculation and identification are limited by the growth period, in order to reduce the workload, the wheat cultivars or lines used in indoor identification are not resistant or highly susceptible cultivars or lines, that is, materials that are not typical resistant or susceptible will no longer undergo field identification;
In the resistance evaluation, R, SS, MS, and HS represent resistant, slightly susceptible, moderately susceptible, and highly susceptible, respectively;
Texts in bold (rows 2, 28 and 71) represent the three lines identified resistant to black point disease.

The formulation and method for preparation of the potato dextrose agar (PDA) medium used in the above examples to cultivate the pathogen B. sorokiniana are as follows.

Formula of PDA medium: potato 200 g, glucose 20 g, agar powder 20 g and tap water 1000 mL, having a natural pH.

Preparation steps: Peeling and washing the potatoes, slicing the potatoes into small chips with a thickness of about 0.2 mm, placing the chips in boiling water and cooking the potato chips to an extent that the chips can be poked through with a glass rod. Then filtering the potato chips with four-layer gauze, and removing the potato chips. Adding glucose and agar powder, continuing to heat and stir them to mix, and then making up to 1000 mL with water after cooling the mixture. Dispensing the mixture into 150 mL flasks (90 mL/flask), sterilizing the mixture at 121° C. for 20 minutes. Cooling mixture to approximately 50° C. and pouring into Petri dishes with a diameter of 9 cm (10 mL/dish), the resulting PDA medium is used to culture B. sorokiniana after cooling.

What is claimed is:

1. A method for identifying resistance of wheat to black point disease caused by *Bipolaris sorokiniana* in an indoor environment, comprising the steps of:

a) a step of surface sterilization of wheat seeds, comprising:
selecting full wheat seeds and immersing the wheat seeds in alcohol, and rinsing the wheat seeds with sterilized distilled water following the immersion to generate sterilized wheat seeds;

b) a step of cultivating wheat seedlings from sterilized wheat seeds, comprising:
placing sterilized wheat seeds from step a) in Petri dishes, placing said Petri dishes in an incubator, and then cultivating said sterilized wheat seeds for 10 days;

c) a step of preparing a conidial suspension of *Bipolaris sorokiniana*, comprising:
cutting *Bipolaris sorokiniana* that have been stored in a refrigerator at 4° C. into 0.3 cm$^2$ pieces and inoculating in a potato dextrose agar medium, culturing at 25° C. in the dark to generate a cultured colony, scraping conidia from the cultured colony with a glass slide, rinsing the potato dextrose agar mediums with distilled water to obtain a fungal suspension, and filtering the fungal suspension with gauze to remove mycelial fragments and obtain a conidia suspension;

d) a step of inoculating the conidia suspension on leaves of a wheat seedling and identifying diseased leaves, comprising:

shaking the conidia suspension of *Bipolaris sorokiniana* obtained in step c) and spraying the conidia suspension on leaves of a wheat seedling which has grown to a one-leaf-one-shoot stage in step b), covering the wheat seedling with a transparent plastic cover, and placing the wheat seedling in an incubator and culturing for 10 days at 25° C.;

e) a step of recording identification results, comprising:

recording a percentage of diseased leaf area within a total leaf area of a leaf of the wheat seedling cultivated in step d) on the $10^{th}$ day of inoculation to obtain a percentage of diseased leaf area;

f) a step of calculating black point incidence in wheat, comprising:

calculating a percentage of black point grains from the percentage of diseased leaf area by using the equation $y=-1.0037x+66.1360$; wherein in the equation, y and x are the black point incidence and the percentage of diseased leaf area, respectively, comprising;

g) a step of evaluating resistance to black point disease, comprising:

evaluating resistance of wheat to black point disease caused by *Bipolaris sorokiniana* based on the black point incidence calculated in step f);

wherein in step c), after incubating *Bipolaris sorokiniana* at 25° C. in dark for 7 days, observing the state of conidia production, wherein a gray color of colonies indicates a relatively lower yield of conidia production and a darker color indicates a relatively higher yield of conidia, and continuing the culture process while removing Petri dishes when the colonies become the darker color.

2. The method according to claim 1, wherein in step a), the volume percentage of alcohol is 70% by volume, duration of time for immersion in alcohol is 2 minutes; and wheat seeds are rinsed with sterilized distilled water 3 times.

3. The method according to claim 1, wherein in step a), rinsing wheat seeds with sterilized distilled water comprises adding distilled water and shaking for 5 seconds so as to dissolve the alcohol on the surface of the seeds in the distilled water, thereby preventing alcohol from inhibiting germination of the wheat seeds.

4. The method according to claim 1, wherein in step b), the step of cultivating the wheat seedlings comprises steps of:

i) placing wheat seeds in Petri dishes with a diameter of 9 cm, in which two layers of sterilized filter paper and 4 mL of sterilized distilled water have been added in advance, and placing 5 wheat cultivars or lines in each Petri dish with 15 grains for each cultivar or line;

ii) placing the Petri dishes with the wheat seeds in a 25° C. incubator and culturing the wheat seeds for 3 days in the dark, removing wheat grains with inconsistent germinability, adding 10 mL of sterilized distilled water to each Petri dish, and removing covers of the Petri dishes;

iii) after culturing the wheat seeds for 3 days in the incubator, continuing to incubate the wheat seeds for 7 additional days by alternating a temperature and light cycle in the incubator between a first cycle comprising a temperature of 25° C. and a light duration of 11 hours and a second cycle comprising a temperature of 21° C. and a dark duration of 13 hours.

5. The method according to claim 1, wherein in step c), the step of rinsing the Petri dishes with distilled water and filtering with a gauze comprises washing the Petri dishes with distilled water for at least two times, filtering the fungal suspension with four layers of gauze to obtain the conidial suspension of *B. sorokiniana*, determining concentration of spores in the conidia suspension by using a hemocytometer, and adjusting spore concentration to $1\times10^5$/mL.

6. The method according to claim 1, wherein in step d) the step of culturing the seedlings after inoculation in an incubator comprises: incubating the seedlings in the dark for 24 hours, setting alternating temperature and light cycle of the incubator at a third cycle of a temperature of 25° C. and light for 11 hours and a fourth cycle of a temperature of 25° C. and dark for 13 hours; spraying 3 mL of sterilized distilled water evenly onto cultured seedlings twice a day during the culturing process so as to maintain a humidity required for infection of *Bipolaris sorokiniana* and for development of leaf blight.

7. The method according to claim 1, wherein step of evaluating the resistance of wheat to black point disease in step g) comprises: recording a value of "I" if there are no diseased grains, wherein "I" is considered to be immune, recording a value of "HR" if the black point incidence is from 0.1% to 1.9%, wherein "HR" is considered highly resistant, recording a value of "R" if the black point rate is from 2.0% to 4.9%, wherein "R" is considered to be resistant, recording a value of "SS" if the black point incidence is from 5.0% to 14.9%, wherein "SS" is considered to be slightly susceptible, recording a value of "MS" if the black point incidence is from 15.0% to 30.0%, wherein "MS" is considered to be moderately susceptible, and recording a value of "HS" if the black point incidence is greater than 30%, wherein "HS" is considered to be highly susceptible.

* * * * *